(12) United States Patent
Hoffmann et al.

(10) Patent No.: US 6,670,121 B1
(45) Date of Patent: Dec. 30, 2003

(54) METHODS FOR CHARACTERIZING MRNA MOLECULES

(75) Inventors: Ralf Hoffmann, Schlebusch (DE); Hermann Lübbert, Lützenkirchen (DE); Stefan Zwilling, Schlebusch (DE)

(73) Assignee: Biofrontera Pharmaceuticals GmbH, Leverkusen (DE)

( * ) Notice: Subject to any disclaimer, the term of this patent is extended or adjusted under 35 U.S.C. 154(b) by 0 days.

(21) Appl. No.: 09/622,247

(22) PCT Filed: Feb. 16, 1999

(86) PCT No.: PCT/EP99/00992

§ 371 (c)(1),
(2), (4) Date: Oct. 24, 2000

(87) PCT Pub. No.: WO99/42610

PCT Pub. Date: Aug. 26, 1999

(30) Foreign Application Priority Data

Feb. 17, 1998 (DE) .......................... 198 06 431

(51) Int. Cl.$^7$ ........................... C12Q 1/68; C12P 19/34; C12N 9/00; C07H 21/04
(52) U.S. Cl. ...................... 435/6; 435/91.2; 435/91.51; 435/91.52; 435/183; 536/25.4
(58) Field of Search ............................. 435/6, 91.2, 183, 435/91.51, 91.52; 536/25.4

(56) References Cited

U.S. PATENT DOCUMENTS

| | | | | |
|---|---|---|---|---|
| 5,665,547 A | * | 9/1997 | Pardee et al. ................. | 435/6 |
| 5,792,851 A | * | 8/1998 | Schuster et al. ............ | 536/23.5 |
| 5,876,932 A | | 3/1999 | Fischer .......................... | 435/6 |

FOREIGN PATENT DOCUMENTS

| | | | |
|---|---|---|---|
| EP | 0 735 144 A1 | 10/1996 | ............ C12Q/1/68 |
| EP | 0 743 367 A2 | 11/1996 | ............ C12Q/1/68 |
| WO | WO 94/01582 | 1/1994 | ............ C12Q/1/68 |
| WO | WO 95/13369 | 5/1995 | ............ C12N/15/11 |
| WO | WO 97/05286 | 2/1997 | ........... C12Q/11/68 |
| WO | WO 97/28282 | 8/1997 | ............ C12Q/1/68 |
| WO | WO 97/29211 | 8/1997 | ............ C12Q/1/68 |

OTHER PUBLICATIONS

Liang, P. et al., "Differential Display of Eukaryotic Messenger RNA by Means of the Polymerase Chain Reaction," (1992) Science 257, pp. 967–971.

Mendelman, L.V. et al., "Base Mispair Extension Kinetics," (1990) J. Biol. Chem., vol. 265, pp. 2338–2346.

Matz, M. et al., "Ordered differential display: a simple method for systematic comparison of gene expression profiles," (1997) Nucl. Acid. Res., vol. 25, pp. 2541–2542.

Prashar, Y. et al., "Analysis of differential gene expression by display of 3' end restriction fragments of cDNAs," (1996) Proc. Natl. Acad. Sci. USA, vol.93, pp. 659–663.

Kato, K., "RNA fingerprinting by molecular indexing," (1996) Nucl. Acids Res., vol. 24, pp. 394–395.

Janulaitis, A. et al., "Purification and properties of the Eco571 restriction endonuclease and methylase–prototypes of a new class (type IV)," (1992) Nucleic Acids Res., vol. 20, pp. 6043–6049.

Petrusyte, M. et al., "Restriction endonucleases of a new type," (1988) Gene 74, pp. 89–91.

Cummins, L., et al., "Characterization of fully 2'–modified oligoribonucleotide hetero– and homoduplex hybridization and nuclease sensitivity," (1995) Nucl. Acids Res., vol. 23, pp. 2019–2024.

Velculescu, V. et al., "Serial Analysis of Gene Expression," (1995) Science, vol. 270, pp. 484–487..

Unrau, P. et al., "Non–Cloning amplification of specific DNA fragments from whole genomic DNA digests using DNA 'indexers'," (1994) Gene, vol. 145, pp. 163–169.

Kato, K., "Description of the entire mRNA population by a 3' end cDNA fragment generated by class IIS restriction enzymes," (1995) Nucl. Acids Res. vol. 23, pp. 3685–3690.

* cited by examiner

*Primary Examiner*—Jeffrey Siew
*Assistant Examiner*—Joyce Tung
(74) *Attorney, Agent, or Firm*—Kilpatrick Stockton LLP

(57) ABSTRACT

The invention relates to methods for the qualitative and quantitative determination of differentially expressed mRNA molecules. Said methods are used especially to determine all possible mRNA molecules present in a cell or a tissue, and to compare them with other cells or tissues, with other conditions (stages of disease or development), or with stages of treatment for these conditions. The method provided for in the invention therefore makes it possible, for example, to establish a comprehensive map of the different mRNA molecules present in a defined mRNA population and subsequently to use the preferably digital information obtained in this way in data base analyses.

27 Claims, No Drawings

METHODS FOR CHARACTERIZING MRNA MOLECULES

PRIOR RELATED APPLICATIONS

The present application is a National Phase of PCT/EP99/00992, filed Feb. 16, 1999, which claims priority to German Patent Application No. 198 06 431.4, filed Feb. 17, 1998.

The present invention relates to methods for the qualitative and quantitative detection of differentially expressed mRNA molecules. The technique on which the invention is based is referred to hereinafter as DEPD (digital expression pattern display) for short.

According to current estimates, the genome of higher organisms comprises about 100,000 different genes, of which, however, only a comparatively small number is expressed in each cell of an organism and thus converted into polypeptides and proteins. It is assumed that substantially all processes and metabolic functions in the realm of living material depend on which genes are switched on or off at which time in which tissues. Thus, numerous findings indicate that cellular processes such as, for example, homeostasis, reactions to allergies, regulation of the cell cycle, ageing and entry of cells into programmed cell death (apoptosis) are based on the differential expression of particular genes or are connected thereto. Both the progress of normal development and the pathological manifestations leading to diseases such as, for example, cancer are essentially based on changes in the expression of genes.

Accordingly, there is a need for specific methods for detecting differently or differentially expressed mRNA molecules in order to identify differences in the expression of genes by comparison with suitable controls. Methods of this type would be of great importance both diagnostically and in the evaluation of therapeutic targets.

The novel method is used in particular for detecting as many as possible of the mRNA molecules present in a cell or in a tissue, and comparison thereof with other cells or tissues or with particular conditions (stages of disease or development) or treatment phases, in particular preferably both in qualitative and in quantitative respects. The novel method thus permits, for example, the construction of a comprehensive picture of the various mRNA molecules present in a defined mRNA population, and the subsequent use of the information obtained thereby, which is preferably digital, in database analyses. It is to be assumed that in the near future all human gene sequences will be available in appropriate databases. The present method therefore permits complete detection and characterization of cellular processes which are reflected by specific expression patterns at the level of the mRNA populations. It is possible thereby, for example, to identify quickly and reliably changes in the expression pattern of individual genes involved in a specific process. This makes it possible also to define novel targets for the essential action of active pharmaceutical ingredients. The resulting information can also be employed for producing the causal connection between known target genes and target proteins via comprehensible biochemical signal and synthesis routes.

The object stated above is known to the person skilled in the relative area. Various routes have been followed in the prior art to achieve the stated object.

For example, P. Liang and A. B. Pardee describe a method for separating individual mRNAs by a polymerase chain reaction (PCR) (P. Liang & A. B. Pardee 1992 Science 257, 967–971). This method was used in order to compare the mRNA populations expressed by two related cell types. Separation of the complex mixture of mRNA molecules into fractions each consisting of 50–100 genes of the total population was achieved by: 1) reverse transcription of the mRNA into single-stranded cDNA with 12 so-called 3' anchor primers of the form $T_{11}VN$ (where $T_{11}$=eleven consecutive Ts, V=A, C, G; N=A, C, G, T); 2) PCR amplification of each individual cDNA fraction with the appropriate 3' anchor primer and an arbitrarily selected 5' oligomer comprising 10 nucleotides in the presence of radiolabelled deoxyribonucleotides. The products were fractionated on sequencing gels, and 50–100 bands were observed in the 100–500 nucleotide size range. The bands resulted from the amplification of cDNAs which correspond to the 3' ends of mRNAs which contained the complement of the 3' anchor primer and of the arbitrarily selected 5' oligomer. The patterns of the bands amplified from the two cDNAs were similar for each primer pair, and it was not possible to differentiate the intensities of about 80% of the bands. Certain bands appeared more strongly in one or other PCR mixture, while some were detectable in only one of the two mixtures.

If all the 50,000–100,000 different mRNAs expected for mammals were detectable using the arbitrarily selected 5' primers (arbitrary primer), then a number of 80–95 such oligonucleotides and about 1000 PCRs would be necessary in order to detect with high probability about two thirds of these mRNAs. It has emerged from numerous investigations in recent years that the method described above leads to a high rate (up to 90%) of false-positive signals.

WO 95/13369 discloses a method (TOGA–TOtal Gene Expression Analysis) for simultaneous identification of differentially expressed mRNAs and for measurement of their relative concentrations. The method is based on the construction of double-stranded cDNA from isolated mRNA using a specific set of oligo (dT) primers. This entails employing a mixture of 12 anchor primers with the following structure: starting from 5', a "stuffer" or "heel" fragment of 4–40 bases is followed by a recognition sequence for a restriction endonuclease (typically NotI), 7–40 dT nucleotides and finally two "anchor bases" V, N at the 3' end of the primer. In this case, V is a deoxyribonucleotide of the group dA, dC or dG, while N defines the deoxyribonucleotides dA, dC, dG and dT. The cDNA obtained in this way is subsequently completely digested with a restriction enzyme which recognizes 4 bases as sequence for the cleavage site (for example MspI), cut with NotI and cloned into an appropriately treated plasmid vector. The orientation of the insert in this case is antisense relative to a vector-encoded, bacteriophage-specific promoter (typically T3). The ligations are transformed into an E. coli strain, whereby cDNA banks are generated. The plasmid DNA of these cDNA libraries is isolated and linearized by means of combination digestions by 6 different restriction enzymes which are different from those used above. The linearized cDNA is translated by T3 polymerase into cRNA and consequently transcribed into 16 subfractions of single-stranded cDNA. This entails use of a thermostable reverse transcriptase at high temperature and one of each of 16 different cRNA primers whose two 3' nucleotides consist of a complete permutation of the 4 possible deoxyribonucleotides dA, dC, dG and dT. The products of the 16 cDNA fractions are employed as templates for PCR with use of a 3' oligonucleotide which corresponds to a vector sequence near to the cloning site of the insert, and of a 5' oligomer which corresponds to one of the 16 cDNA synthesis primers with addition of two 3' nucleotides of the complete permutation of the 4 possible deoxyribonucleotides dA, dC, dG and dT. Up to 256 different pools are generated in this way, and the radiolabelled bands (35S-dATP or 32P-dCTP) thereof are analysed on polyacrylamide gels. It is said to be theoretically possible on the basis of the information obtained about the length and composition of the 8 identified bases in a labelled band to conclude the identity of the relevant gene in a complete database without cloning and sequencing steps.

The method described above gives rise to the following problems in connection with the high specificity, selectivity and reproducibility which are desired according to the invention:

1) potential loss of cDNA sequences through NotI digestion;
2) potential loss of cDNA sequences through vector ligation;
3) potential loss of cDNA sequences through transformation into *E. coli* and different amplification rates for different cDNA inserts;
4) contamination of the PCR templates with bacterial genomic DNA after plasmid amplification and purification from *E. coli*;
5) contamination of the templates for the T3 RNA polymerase reaction with insert-free plasmid DNA;
6) loss of cDNA inserts through combined linearization digestions with 6 different restriction endonucleases;
7) loss of cDNA sequences through cRNA synthesis amplification;
8) loss of cDNA sequences through the second cDNA synthesis amplification;
9) doubtful specificity of the thermostable reverse transcriptase for the permutated primers employed for the second cDNA synthesis, because the selectivity of the reverse transcriptase in the case of base mispairing is generally about 10–1000 times (for AMV RT) less than the selectivity of Taq polymerase (L.V. Mendelman et al. 1990, J. Biol. Chem. 265, 2338–2346);
10) Doubtful selectivity of the Taq polymerase for the permutated 5' oligomers used in the PCR under the described conditions, because base mispairings are tolerated with the primers employed. Correct analysis of the information is thus not ensured.

M. Matz et al. describe another method (ODD—ordered differential display—1997, Nucl. Acid. Res. 25, 2541–2542) for identifying differentially expressed genes, which is based on PCR amplification by adaptor-specific oligonucleotides and the PCR suppression effect. In this case, double-stranded cDNA is generated using an oligonucleotide of the structure "heel-dT(13)", where "heel" is a sequence of 12 bases. The cDNA is completely digested by a restriction enzyme with a recognition sequence comprising 4 bases (RasI) and ligated to a "pseudo double-stranded adaptor". This molecule consists of a longer (39 bases) and of a shorter (12 bases complementary to the 3' end of the longer) oligomer, which are hybridized together under suitable conditions. The 5' ends of the oligo-nucleotides are not phosphorylated in this case. Theoretically, specific amplification of the 3' ends of the cDNA is possible in this way in a 1st PCR using the cDNA synthesis primer and a primer which corresponds to the 5' end of the longer adaptor oligomer, with a high annealing temperature in the PCR (65° C.). Fractionation of the complex cDNA into different fractions is a achieved in a 2nd PCR. This entails use of the cDNA synthesis primer with the addition of two 3' nucleotides of the complete permutation of all four deoxyribonucleotides dA, dC, dG and dT and primer which corresponds to the 3' end of the longer adaptor oligomer with the addition of two 3' nucleotides of the complete permutation of all four deoxyribonucleotides dA, dC, dG and dT. To increase the specificity of the adaptor primer, an artificial mispairing (mismatch) was introduced into the oligonucleotide at position −4 relative to the 3' end of the primer.

The method described above gives rise to the following problems in connection with the high specificity, selectivity and reproducibility desired according to the invention:

1) the use of a non-anchored cDNA synthesis primer does not allow reproducibility of the fragment lengths found to be guaranteed;
2) amplification of the 3' ends of the cDNA using an oligomer of the structure "heel-dT(13)" with high annealing temperatures in the PCR is not reproducible;
3) selective amplification of the 3' ends of the cDNA through use of a "pseudo double-stranded adaptor" is not ensured;
4) the increased specificity in the 2nd PCR for the permutated 5' oligonucleotides through the introduction of one artificial mismatch is unsatisfactory;
5) the 3' oligomers employed in the 2nd PCR contain no artificial mismatch and are therefore insufficiently selective for the primer permutation;
6) due to the specific arrangement of the PCR, the information obtained from the gel analysis about the individual DNA fragments (fragment length and 6 known nucleotides) is insufficient without additional cloning and sequencing steps.

Y. Prashar and S. Weissman (1996, Proc. Natl. Acad. Sci. USA 93, 659–663) describe a method in which double-stranded cDNA is prepared using 12 oligonucleotides having the following structure: starting from 5' a "heel" structure is followed by a sequence of 18 dT nucleotides and two "anchor bases" V, N at the 3' end of the primers. In this, V is a deoxyribonucleotide of the group dA, dC or dG, while N defines the deoxyribonucleotides dA, dC, dG and dT. The cDNA synthesis takes place at a temperature of 50° C. and is intended to make it possible to divide the complex mixture into 12 different pools. After complete digestion of the cDNA with various restriction endonucleases which recognize six nucleotides as sequence for the cleavage site, the resulting DNA fragments are provided with an adaptor which has the structure of a Y. In the subsequent PCR there is use of a 3' primer which binds to the "heel" structure of the cDNA. The 5' primer employed is an oligonucleotide, the binding site of which is located in the outer region of the Y adaptor, and which is produced only when the complementary strand to this region is formed in a first synthesis. All the fragments having a Y adaptor on both sides are unable to undergo amplification.

The fractionation, asserted by the authors, of the cDNA products into different fractions is not reproducible due to the cDNA synthesis primer used, which is permutated at the 3' end. In addition, owing to the use of the specific adaptor structure, no permutated PCR 5' primers can be employed.

WO 97/29211 describes the technique of "restriction display (RD-PCR)", in which double-stranded cDNA is prepared using 12 oligonucleotides. These primers have the following structure: starting from 5' a "heel" structure is followed by two deoxynucleotides of the complete permutation of all four deoxynucleotides dA, dC, dG and dT, a sequence of 17 dT nucleotides and two "anchor bases" V, N at the 3' end of the primer. In this, V is a deoxyribonucleotide of the group dA, dC or dG, while N defines the deoxyribonucleotides dA, dC, dG and dT. After complete digestion of the cDNA with one or more restriction endonucleases, an adaptor molecule is ligated to the cDNA fragments. In a subsequent PCR there is use of a 3' primer which binds selectively to the "heel" structure of the cDNA and additionally has two 3' nucleotides V, N at the 3' end of the primer. In this, V is a deoxyribonucleotide of the group dA, dC or dG, while N defines the deoxyribonucleotides dA, dC, dG and dT. The 5' primer employed is an oligonucleotide corresponding to the 3' sequence of the adaptor primer and additionally having a 3' nucleotide or two 3' nucleotides or three 3' nucleotides with the complete permutation of all four deoxyribonucleotides dA, dC, dG and dT. The PCR is in this case carried out with various permutation combinations so that in a first PCR (or in the first 10–25 PCR cycles) 5' primers with only one permutation are employed, and then in a second PCR (or in the remaining PCR cycles) 5' primers with only two or three permutations are employed. This is intended to increase markedly the selectivity for the various 5' primer permutations.

The method described above gives rise to the following problems in connection with the high specificity, selectivity and reproducibility desired according to the invention:

1) the use of various cDNA synthesis primers with 3' permutations is not selective and therefore does not permit the reproducibility of the method to be guaranteed;

2) the division of the amplification step into several PCR rounds with 5' primers which have a different number of 3' permutations is not sufficiently sequence-selective on its own for the technique to be employed, for example, in a database-oriented gene expression analysis.

Kato describes a method ("molecular indexing" 1995, Nucl. Acids Res., Vol. 23, 3685–90 and 1996, Nucl. Acids Res., Vol. 24, 394–95), which is based on the digestion of the double-stranded cDNA with class IIS restriction endonucleases. These generate 5' overhangs of the cDNA of unknown sequence. Then, 64 biotinylated adaptors whose nucleotides 2–4 (relative to the 5' end) of their 5' overhangs are complementary to in each case one 64th of the complete cDNA pool are ligated with DNA ligase from E. coli. The particular 5' nucleotide of the adaptor overhangs remains undefined. The cDNA fragments ligated in this case are purified via binding to streptavidin-coupled magnetic particles. In a subsequent PCR, the adaptor-ligated 3' ends of the cDNA are amplified using an adaptor oligonucleotide and an oligo-(dT) oligomer which is expanded at the 3' end by one of the three nucleotides dA, dC or dG, at low annealing temperature. The cDNA is fractionated into 192 different pools in this way. This method also gives rise to the following problems in connection with the high specificity, selectivity and reproducibility desired according to the invention:

1) the ligation of adaptors with four nucleotides as 5' overhang is not permutation-specific enough, without further after-treatment, to be able to determine with certainty the first three or four bases of the cDNA insert;

2) in order to achieve maximal ligation specificity, only a very small quantity of adaptor molecule is employed in the ligation, but this leads to distinctly reduced ligation efficiency. The consequence of this in turn is that the sensitivity of the overall method is reduced;

3) the division of the cDNA into pools using anchored oligo-(dT) primers cannot be carried out successfully with a low annealing temperature in the PCR.

Because of the outlined disadvantages of the prior art techniques described above, especially in relation to the lack of or only low reproducibility and sequence-specificity during the PCR amplification of the 3' ends of the cDNA, there is a need to develop and establish a method which is distinctly superior to the known methods in relation to specificity, selectivity, sensitivity and reliable reproducibility, and reduced rate of error for the results obtained. These criteria are particularly necessary when, for example, a database-assisted analysis is to be carried out for differential gene expression by means of a digital display.

Thus, according to the invention, a method for identifying and characterizing mRNA molecules is provided and comprises the following steps:

(a) isolation and purification of polyA RNA from tissue samples;

(b) synthesis of double-stranded cDNA from the mRNA molecules;

(c) truncation of the cDNA by enzymatic digestion with restriction endonucleases;

(d) hybridization and ligation of adaptor molecules to the cut cDNA;

and either, in a 1st alternative, (e) filling-in of the 5' overhangs of the cDNA with deoxyribonucleotides and Klenow DNA polymerase;

(f) selective purification of the 3' ends of the cDNA;

(g) removal of the 3'-poly-dA nucleotides from the cDNA by enzymatic digestion with a restriction endonuclease;

(h) hybridization and ligation of adaptor molecules to the cut cDNA;

(i) amplification of the cDNA fragments by PCR (polymerase chain reaction);

(j) fractionation of the amplification products according to their length;

(k) analysis of the amplification products; or, in a 2nd alternative, (e) selective purification of the 3' ends of the cDNA;

(f) removal of the 3'-poly-dA nucleotides from the cDNA by enzymatic digestion with a restriction endonuclease;

(g) hybridization and ligation of adaptor molecules to the cut cDNA;

(h) amplification of the cDNA fragments by PCR (polymerase chain reaction), using 5' primers which have two or three permutations at the 3' end, and which contain one or two artificial mismatches compared with the complementary strand defined by the adaptor molecules;

(i) fractionation of the amplification products according to their length;

(j) analysis of the amplification products; or, in a third alternative, (e) amplification of the cDNA fragments by PCR (polymerase chain reaction), using 5' primers which have two or three permutations at the 3' end, and which contain one or two artificial mismatches compared with the complementary strand defined by the adaptor molecules;

(f) fractionation of the amplification products according to their length;

(g) analysis of the amplification products; where for the $1^{st}$ and $2^{nd}$ alternative in step (b) the synthesis of the first strand cDNA molecules takes place by reverse transcription using an anchored oligo-dT nucleotide which has a 3' extension of 2 bases, where the first base is dA, dC or dG, and the second base is dA, dC, dG or dT, and which has a 5' extension of 5–15, preferably 6–15, bases, which codes for the cleavage site of a restriction endonuclease with the cleavage characteristics 16/14 nucleotides downstream of the recognition sequence; or where for the 3rd alternative in step (b) the synthesis of the first strand cDNA molecules takes place by reverse transcription using an anchored oligo-dT nucleotide which has a 3' extension of 2 bases, where the first base is dA, dC or dG, and the second base is dA, dC, dG or dT, and which has a 5' extension of 5–15 bases of any sequence.

Enzymes with the cleavage characteristics 16/14 nucleotides downstream of the recognition sequence are known to the skilled worker. For example, Eco57I and BsgI (see, for example, A. Janulaitis et al., Nucleic Acids Res. 20 (1992), pp. 6042–6.049; Petrusyte et al., Gene 74 (1988), pp. 89–91).

It is preferred in the novel method for the oligo-dt nucleotide to be completely substituted by 2'-O-methylated ribonucleotides. Alternatively, the oligo-dt nucleotide may consist of standard deoxyribonucleotides.

It is further preferred in the novel method for the oligo-dT nucleotide to be provided at its free 5' end and/or on internal dT nucleotides with a biotin residue via a C9 spacer.

A preferred embodiment relates to a novel method where in step (h) of the 2nd alternative or step (e) of the 3rd alternative the mismatches are located at positions –3, or –3 and –4, or –4 and –5, compared with the complementary strand defined by the adaptor molecules.

A further preferred embodiment of the novel method is characterized in that in step (c) there is use of a class IIS restriction enzyme which has 5 nucleotides as recognition sequence and generates an overhang consisting of 2–4, in particular 4, nucleotides, which are not part of the recognition sequence, of the cut cDNA fragments.

A further preferred embodiment of the novel method is characterized in that in step (f) of the 1st alternative or in step (e) of the 2nd alternative the selective purification of the 3' ends of the cDNA takes place using paramagnetic beads which have coupled the biotin-binding molecule streptavidin.

A class IIS restriction enzyme is preferably used in step (g) of the 1st alternative or in step (f) of the 2nd alternative of the novel method.

It is further preferred to incubate the products from step (d) or from step (h) of the 1st alternative or from step (g) of the 2nd alternative of the novel method before the amplification in step (i) with a nuclease selected from the group consisting of T4 endonuclease VII, S1 nuclease, and mung bean nuclease.

The novel method is further preferably characterized in that in step (i) of the first alternative or in step (h) of the 2nd alternative or step (e) of the 3rd alternative the amplification of the cDNA fragments takes place using oligonucleotides which hybridize onto the complementary strand of the sense oligomer of the ligated adaptor molecules.

The novel method is further preferably characterized in that in step (k) of the first alternative or in step (j) of the 2nd alternative or step (g) of the 3rd alternative the analysis takes place on the basis of the different lengths of the products and with knowledge of the base sequence of 9 or 10 nucleotides which is known through the manipulation.

A further preferred embodiment relates to the use of the novel method according to any of the preceding claims [sic] for the optionally computer-assisted identification and isolation, and analysis, of new genes.

The novel DEPD method was developed in order to reduce markedly the rate of errors in the identification of some nucleotides in the cDNA fragments which in turn permit identification of the encoded gene in a suitable database. The improved efficiency of the novel method derives from the use of specific ligation techniques in suitable combination with permutation-specific mismatch PCR. This entails ligation of an adaptor molecule to the 5' end and 3' end of the fragments after selective purification of the 3' ends of the cDNAs. The primers employed in the subsequent PCR preferably each have two bases as permutation. The permutation-specificity of the PCR primers can be distinctly increased at a high annealing temperature and, preferably, with simultaneous introduction of artificial template mismatches at selective oligonucleotide sites.

Owing to the novel combination of a plurality of individual steps employed to determine nucleotide sequences by PCR, a synergistic effect in relation to the specificity of the technique emerges. The result is a type of control mechanism for the individual procedures, because every error occurring, for example, in the ligation can be corrected by the selective PCR by means of mismatch primers. The permutation selectivity of the PCR has been distinctly increased by the preferred introduction of defined template mismatches.

In another preferred embodiment, the use of permutation primers on both sides of the cDNA template results in an error-correcting effect because those amplification products erroneously produced by means of one oligomer in one of the first PCR rounds can have their further replication suppressed if the opposite primer amplifies only the correct permutation. It is furthermore possible in another preferred embodiment to define, through suitable, combined use of ligation and PCR permutation techniques in the DEPD method, 9 or 10 nucleotides and the length of an amplified fragment. This information ought to be sufficient for reliable identification of a gene, preferably by database analysis, even if an error were to result in the determination of the base sequence of the cDNA fragment.

Use of the novel DEPD method makes it possible inter alia to analyse comprehensively the interplay of all the genes involved in a defined system and/or in a defined situation at the level of the mRNA expression pattern, with only small amounts of tissue or cells being required for specific and reproducible results. The method can be employed in a large number of applications. These include, for example, comparison of organs, tissues, tissue parts, or of diseased tissues or tissue parts with corresponding healthy material, where appropriate also within the framework of a comparative investigation using active pharmaceutical ingredients versus corresponding controls without administration of active ingredient. The novel method also makes it possible to compare defined conditions in animal models, particular preference being given here to comparative analyses of organs, tissues, tissue parts or diseased tissues or tissue parts versus corresponding healthy material. Further applications relate to the analysis of transgenic animals, which also include so-called knock-out animals, and phenotypical evaluation of the use of antibodies, antisense and ribozyme oligonucleotides and comparable means employed within the framework of functional approaches to elucidating the relevance of particular genes.

The use of such a technique allows the speed of screening of investigational material to be distinctly increased because isolation of differentially expressed genes with subsequent cloning and sequencing is no longer necessary. It is therefore possible to investigate a much larger number of samples or far more different stages of a sample (for example time courses of changes of gene expression over several hours/days etc.). This is important not only in relation to the discovery of new possible drug targets, but also in particular in relation to elucidating the mechanisms of action of potential therapeutic substances, because in this case particularly large amounts of sample material may result from detailed investigation.

A further aspect of the present invention is its preferred use within the framework of a database oriented gene expression analysis method. In contrast to the enormous technical complexity of currently established methods of similarly high efficiency such as, for example, the chip hybridization technology (for example Affymetrix, USA) from the production of the chips via the technique of analysing the chip hybridization and onto the automated data analysis, the novel method represents a surprisingly simple and cost-efficient alternative which is qualitatively distinctly superior to known methods of the type described at the outset.

The novel method and preferred embodiments thereof will be described in detail hereinafter. Concerning detailed information on established standard methods, reference is made, for example, to J. Sambrook et al. 1989: Molecular Cloning: A Laboratory manual, Cold Spring Harbor Laboratory Press, Cold Spring Harbor, N.Y.

EXAMPLES 1) mRNA Isolation

Isolation and purification of complete RNA from tissues, tissue parts, biopsy samples, cells etc. to be investigated takes place by described standard methods. For complete removal of possible contamination of the isolated RNA by genomic DNA, an enzymatic digestion with DNaseI (Boehringer Mannheim, Germany) is carried out. This is followed by purification of polyA mRNA from the total RNA by means of oligo(dT)-coupled magnetic particles (Oligo(dT) magnetic beads, Promega, Wis., USA).

2) cDNA Synthesis

Double-stranded cDNA is synthesized from mRNA using a mixture of 12 anchor primers with the following structure: starting from 5' , a "heel" fragment (5' extension) of 5–15 bases, for example 5 or 6 bases, is followed by a recognition sequence for one of the restriction enzymes BsgI or Eco57I. This is followed by a sequence of 14 dT nucleotides and the two anchor nucleotides V, N at the 3' end of the primer. In this case, V is a deoxyribonucleotide of the group dA, dC or dG, while N defines the deoxyribonucleotides dA, dC, dG and dT. The deoxyribonucleotides the dT sequence and, where appropriate, of the "heel" fragment are in this case completely substituted by 2'-O-methylated ribonucleotides. The cDNA synthesis primer is provided at the 5' end and/or on one or more internal dT nucleotides with a biotin residue (C9 spacer).

Alternatively, the cDNA synthesis can be carried out with a mixture of 12 unmodified, i.e. consisting of deoxyribonucleotides, anchor primers instead of with 2'-O-methylated ribonucleotides.

3) First Digestion of the cDNA With Restriction Endonucleases

Complete digestion of the cDNA with a type IIS restriction enzyme which recognizes 5 bases as sequence for the cleavage site (for example: FokI, Bsm AI, Bsm FI or Bbv I) and generates two to four unknown nucleotides as overhang of the cDNA. The enzymes mentioned by way of example in the further statements generate a nucleotide overhang of 4 bases. With shorter overhangs it is necessary to truncate appropriately the adaptors to be ligated.

4) First Adaptor Ligation a) The enzymic digestion produces a 5' overhang of four unknown nucleotides in the cDNA. Sixteen adaptor molecules consisting of two oligomers (not 5'-phosphorylated, "pseudo double-stranded" adaptors) are ligated to the cDNA after the restriction digestion has taken place. The adaptor typically consists of two oligonucleotides of different lengths, the longer consisting of 25–35 and the shorter (complementary to the 3' end of the longer one) consisting of 8–25 bases, in particular 8–12 bases. The adaptor is produced by hybridization of the two oligonucleotides together under suitable conditions and forms a 4-nucleotide overhang, it being possible for nucleotide 3 or 4 ("inner" nucleotides—relative to the 5' end of the antisense oligomer) to be one of the four possible deoxyribonucleotides dA, dC, dG and dT, with the "outer" nucleotides 1 and 2 (relative to the 5' end of the antisense oligomer) remaining undefined, i.e. always consisting of a mixture of the complete combination of all four deoxyribonucleotides. This results in 16 permutated adaptors whose "inner" two nucleotides determine the specificity of the ligation. To ensure correct adaptor ligation, the ligation mixtures are subsequently incubated with a nuclease selected from the group consisting of T4 endonucleases VII, S1 nuclease, and mung bean nuclease.

Ligation of the 16 permutated adaptor molecules takes place at 4–37° C., 1–16 hours, 0–150 mM Na acetate, 1–5 units of T4 DNA ligase (or Taq DNA ligase or *E. coli* DNA ligase) in a suitable buffer. Each of the 16 ligation mixtures is employed as template in a PCR after purification (see (8a)).

b) Alternatively, 64, instead of 16, different "pseudo double-stranded" adaptors which form a 4-nucleotide overhang are finally ligated to the cDNA. In this case, the 64 adaptor overhangs are composed of all deoxyribonucleotide combinations of bases 2–4 (relative to the 5' end of the antisense oligomer), while the "outer" nucleotide (relative to the 5' end of the antisense oligomer) is employed as a mixture of all four nucleotides. This means that the "inner" three nucleotides determine the specificity of the ligation. This method is based on the realization that the DNA ligase from *E. coli* is able to discriminate between the first three bases of the adaptor overhang in the ligation. This takes place under the conditions already described above. To ensure correct adaptor ligation, the ligation mixtures are subsequently incubated with a nuclease selected from the group consisting of T4 endonuclease VII, S1 nuclease, and mung bean nuclease.

c) Alternatively, instead of ligation of 16 or 64 different "pseudo double-stranded" adaptors, the 5-overhangs of the cDNA are filled in successively with deoxyribonucleotides using Klenow DNA polymerase. This is possible through use of dideoxyribonucleotides (ddNTP) and competitive adaptor molecules. In addition, the 3' ends of the cDNA are not eluted from the magnetic particles in order to be able to remove after each step the nucleotides employed. If, for example, the base overhang 5'-GGTT-3' is to be filled in, the cDNA is incubated firstly with ddC nucleotides in order to block all overhangs starting with a dG. After removal of the didexoribonucleotides [sic], the cDNA is incubated with dA nucleotides. This is followed by ligation of an adaptor molecule which has a blunt and a sticky end to those cNDAs [sic] which have a filled-in 5' overhang until then. In the same step, two competitive adaptor molecules are ligated. These likewise have a sticky end and a 5' overhang consisting of one dC or three dC molecules. These block the cDNA 5' overhangs 5'-GTTT-3' and 5'-GGGT-3' respectively. This is followed by further purification of the streptavidin-bound cDNA fragments, which is [sic] then incubated with dC nucleotides. Subsequently there is ligation of an adaptor molecule with a blunt end, which is able to ligate only to the completely and correctly filled-in cDNA. In this way, each of the 256 possible cDNA 5' overhangs are completely filled in with DNA polymerase and then employed in a PCR.

5) Selective Purification of the 3' Ends of the cDNA

To ensure selective amplification of the 3' ends of the cDNA, these fragments are specifically purified from the complete pool of complex cDNA. The 3' ends of the cDNA can be selectively purified from the cDNA mixture preferably with the aid of magnetic particles (magnetic beads), which are coupled to streptavidin (see also Biomagnetic Techniques in Molecular Biology, Dynal, N-0212 Oslo, Norway). This type of purification ensures that in the subsequent PCR there is no non-specific amplification of internal (i.e. not 3' ends) cDNA fragments. Elution of the cDNA from the magnetic particles takes place either by extraction with organic solvents at high temperature (65° C.) or by enzymatic digestion with one of the restriction endonucleases BsgI or Eco57I (see below).

6) Second Digestion of the cDNA With Restriction Endonucleases for Alternative (4b)

Complete digestion of the ligated cDNA with one of the restriction enzymes BsgI or Eco57I. In this case, the oligo-dT nucleotides of the 3' end of the cDNA are completely eliminated and a 2-nucleotide overhang of the last two 3' bases (V, N) of the cDNA, which are located 5' relative to the poly-dA stretch of the mRNA, is generated.

7) Second Adaptor Ligation for Alternative (4b)

In each case, four adaptor molecules consisting of two oligomers are, after restriction digestion has taken place, ligated to in each case one ligation mixture from (4b). The adaptor typically consists of two oligonucleotides of different lengths, the longer consisting of 25–35 and the shorter (complementary to the 3' end of the longer one, 5'-phosphorylated) consisting of 22–30 bases. The adaptor is produced by hybridization of the two oligonucleotides together under suitable conditions and forms a 2-nucleotide overhang, it being possible for the "outer" 3' nucleotide to be one of the four deoxyribonucleotides dA, dC, dG or, dT, with the "inner" nucleotide being defined from a mixture of the three bases dA, dC or dG. Thus the "outer" 3' nucleotide of the adaptor overhang determines the specificity of the ligation. The ligation conditions are as described above. Each of the 256 ligation mixtures is employed as template in a PCR after purification (see (8b)).

8a) PCR for Alternative (4a)

In a total of 256–1024 PCRs, the 3' primer used is the cDNA synthesis primer (mixture of 12 anchor primers) completely substituted by 2'-O-methylated ribonucleotides. In this case, owing to the increased dissociation temperature of the modified bases of the oligonucleotide it is possible to use a distinctly higher (up to 40%, see, for example, L. L. Cummins 1995, Nucl. Acids Res., 23, 2019–2024) annealing temperature in the PCR than with an unsubstituted primer.

An t of the ligation mixtures generated in (4a) is employed in the PCR. The 5' primers are either in a first PCR round 16–64 oligomers with a length of 18–27 bases which correspond to the 3' end of the sense adaptor oligonucleotide with the addition of two or three 3' nucleotides of the complete permutation of all four deoxyribonucleotides dA, dC, dG and dT. The primer permutations employed in this case correspond to the bases 3–4 or 2–4, which are defined in the ligation mixtures under (4a), of the adaptor overhangs. In a second, subsequent PCR round, a further 16 or 64 PCRs are carried out per first PCR, using the same 3' primer and, in each case, 16 5' oligonucleotides with a length of 18–27 bases which correspond to the 5' primer of the first PCR but are extended by two or three 5' nucleotides of the complete permutation of all four deoxyribonucleotides dA, dC, dG and dT.

To ensure the specificity of the amplification of the various permutations in the PCR, selective PCR primers are used and may contain a plurality of artificially introduced mismatches in relation to the template DNA. These mismatches may be located anywhere in the oligomer, with preference being given to 2 mismatches at positions −2and −3 or 1 mismatch at position −1 relative to the 3' end of the primer (position 0).

The PCR profile is typically: 3 min, 95° C. followed by 20–40cycles with 45 sec, 95° C., 45 sec, 65° C., 60 sec, 72° C. and a final extension for 60 sec at 72° C., and is carried out using radiolabelled or fluorescent-labelled PCR primers.

8b) Further Possibility of a PCR for Alternative (4a)

Alternatively, the PCR is carried as described under 8a) but employing an unmodified cDNA synthesis primer (mixture of 12 anchor primers), consisting of standard deoxyribonucleotides.

8c) PCR for alternative (4b)

In a total of 256 PCRs, 64 5' primers with a length of 18–27 bases which correspond to the 3' end of the sense oligonucleotide of the first ligated adaptor molecule (see (4b)) with the addition of three 3' nucleotides of the complete permutation of all four deoxyribonucleotides dA, dC, dG and dT are used. The primer permutations employed in this case correspond to the bases 2–4, defined in the ligation mixtures under (4b), of the adaptor overhangs. The 3' primers employed are four oligonucleotides with a length of 18–27 bases, which correspond to the 3' end of the sense oligonucleotide of the second ligated adaptor molecule (see (7)).

The PCR profile is typically: 3 min, 95° C. followed by 20–40cycles with 45 sec, 95° C., 45 sec, 65° C., 60 sec, 72° C. and a final extension for 60 sec at 72° C. and is carried out using radiolabelled or fluorescent-labelled PCR primers.

8d) PCR for Alternative (4c)

In a total of 256 PCRs (one PCR for each "filling-in reaction"), a 5' primer with a length of 18–27 bases, which corresponds to the 3' end of the sense oligonucleotide of the ligated adaptor molecule, is employed. The cDNA synthesis oligonucleotide is used as 3' primer. The PCR profile is typically: 3 min, 95° C. followed by 20–40cycles with 45 sec, 95° C., 45 sec, 65° C., 60 sec, 720° C. and a final extension for 60 sec at 720° C. and is carried out in the presence of radiolabelled nucleotides.

9) PCR Analysis

Analysis of the PCR fragments typically takes place on 6% polyacrylamide gels (PAA gels) with 7–8 M urea or by capillary electrophoresis.

It emerges from the results that the selectivity for the amplification of the correct 5' nucleotides of the cDNA is inadequate for the 5' primers of the TOGA method, in particular when it is intended to carry out a computer-assisted database analysis of the results. The error rate in the novel use of the 5' primers is $\leq 5\%$. The error rate can be further reduced to approximately 0% by the ligation method described above. In view of this extremely low error rate, establishment of an automated data analysis is also made possible.

What is claimed is:

1. A method for identifying and characterizing mRNA molecules, comprising the steps of:
   a) isolating and purifying poly-A mRNA from tissue samples;
   b) synthesizing double-stranded cDNA from the poly-A mRNA, wherein a first cDNA strand is synthesized using reverse transcriptase using an anchored oligo-T nucleotide having a 3' extension of two bases, wherein a first base is A, C or G and a second base is A, C, G or T, and having a 5' extension of 5–15 bases, wherein the 5' extension comprises a recognition site for a second restriction endonuclease with cleavage characteristics $16/14$ nucleotides downstream of the recognition sequence, and a second cDNA strand is synthesized using the first cDNA strand as a template to form the double-stranded cDNA;
   c) truncating the double-stranded cDNA with a first restriction endonuclease, thereby forming truncated cDNA fragments;
   d) hybridizing and ligating a first set of adaptor molecules to ends of the truncated cDNA fragments;
   e) purifying 3' ends of the truncated cDNA fragments comprising 3' poly-da nucleotides;
   f) removing 3' poly-dA nucleotides from the ends purified ends of the purified truncated cDNA fragments with the second restriction endonuclease;
   g) hybridizing and ligating a second set of adaptor molecules to the truncated cDNA with removed 3' poly-dA nucleotides;
   h) amplifying the truncated cDNA fragments with removed 3' poly-da nucleotides with a polymerase chain reaction, thereby forming amplification products, wherein 5' primers having two or three permutations at the 3' end and containing one or two artificial mismatches to a complementary adaptor sequence are used in the polymerase chain reaction;
   i) fractionating the amplification products according to their length; and,
   j) analyzing the amplification products.

2. A method for identifying and characterizing mRNA molecules, comprising the steps of:
   a) isolating and purifying poly-A mRNA from tissue samples;
   b) synthesizing double-stranded cDNA from the poly-A mRNA, wherein a first cDNA strand is synthesized using reverse transcriptase using an anchored oligo-T nucleotide having a 3' extension of two bases, wherein a first base is A, C or G and a second base is A, C, G or T, and having a 5' extension of 5–15 bases, wherein the 5' extension comprises a recognition site for a second restriction endonuclease with cleavage characteristics $16/14$ nucleotides downstream of the recognition sequence, and a second cDNA strand is synthesized using the first cDNA strand as a template to form the double-stranded cDNA;
   c) truncating the double-stranded cDNA with a first restriction endonuclease, thereby forming truncated cDNA fragments with overhangs;
   d) adding deoxyribonucleotides to the overhangs of the truncated cDNA fragments with Klenow DNA polymerase followed by blunt ligation of a first set of adaptor molecules;
   e) purifying the truncated cDNA fragments comprising 3' poly-dA nucleotides;
   f) removing 3' poly-dA nucleotides from the ends purified ends of the purified truncated cDNA fragments with the second restriction endonuclease;
   g) hybridizing and ligating a second set of adaptor molecules to the truncated cDNA with removed 3' poly-dA nucleotides;
   h) amplifying the truncated cDNA fragments with removed 3' poly-dA nucleotides with a polymerase chain reaction, thereby forming amplification products;
   i) fractionating the amplification products according to their length; and,
   j) analyzing the amplification products.

3. The method of claim 1, wherein the oligo-T nucleotide in step b is a 2'-O-methylated ribonucleotide.

4. The method of claim 2, wherein the oligo-T nucleotide in step b is a 2'-O-methylated ribonucleotide.

5. The method of claim 1, wherein the oligo-T nucleotide in step b is a deoxyribonucleotide.

6. The method of claim 2, wherein the oligo-T nucleotide in step b is a deoxyribonucleotide.

7. The method of claim 1, wherein in step h the mismatches are located at position 3, and 4, or 4 and 5 nucleotides upstream of the 3' end of the primer.

8. The method of claim 1, wherein the first restriction endonuclease in step c is a class IIS restriction endonuclease having 5 nucleotides as a recognition sequence, the endonuclease generating an overhang of the truncated cDNA fragments, wherein the overhang consists of 2–4 nucleotides which are not part of the recognition sequence for the first restriction endonuclease.

9. The method of claim 2, wherein the first restriction endonuclease in step c is a class IIS restriction endonuclease having 5 nucleotides as a recognition sequence, and wherein the overhang of the truncated cDNA fragments with overhangs consists of 2–4 nucleotides which are not part of the recognition sequence for the first restriction endonuclease.

10. The method of claim 1, wherein in step e the 3' ends of the truncated cDNA fragments are purified using streptavidin-coupled paramagnetic beads.

11. The method of claim 2, wherein in step e the 3' ends of the truncated cDNA fragments are purified using streptavidin-coupled paramagnetic beads.

12. The method of claim 1, wherein the second restriction endonuclease in step f is a class IIS restriction endonuclease.

13. The method of claim 2, wherein the second restriction endonuclease in step f is a class IIS restriction endonuclease.

14. The method of claim 2, further comprising incubating products of step g with a nuclease selected from the group consisting of T4 endonuclease VII, S1 nuclease, and mung bean nuclease prior to amplifying the cDNA fragments in step h.

15. The method of claim 2, further comprising incubating products of step g with a nuclease selected from the group consisting of T4 endonuclease VII, S1 nuclease, and mung bean nuclease prior to amplifying the cDNA fragments in step h.

16. The method of claim 1, wherein analysis in step j includes:
   (i) analysis of lengths of the amplification products determined in step i; and,
   (ii) analysis of 9 or 10 bases of cDNA fragments from prior steps.

17. The method of claim 2, wherein analysis in step j includes:
   (i) analysis of lengths of the amplification products determined in step i; and,
   (ii) analysis of 9 or 10 bases of cDNA fragments from prior steps.

18. The method of claim 1, wherein the oligo-T nucleotide in step b is conjugated at its free 5' end and/or at one or more internal T nucleotides with one or more biotin residues with a C9 spacer.

19. The method of claim 2, wherein the oligo-T nucleotide in step b is conjugated at its free 5' end and/or at one or more internal T nucleotides with one or more biotin residues with a C9 spacer.

20. The method of claim 3, wherein the 2'-O-methylated ribonucleotide is conjugated at its free 5' end and/or at one or more internal T nucleotides with one or more biotin residues with a C9 spacer.

21. The method of claim 4, wherein the 2'-O-methylated ribonucleotide is conjugated at its free 5' end and/or at one or more internal T nucleotides with one or more biotin residues with a C9 spacer.

22. The method of claim 5, wherein the deoxyribonucleotide is conjugated at its free 5' end and/or at one or more internal T nucleotides with one or more biotin residues with a C9 spacer.

23. The method of claim 6, wherein the deoxyribonucleotide is conjugated at its free 5' end and/or at one or more internal T nucleotides with one or more biotin residues with a C9 spacer.

24. The method of claim 1, further comprising use of computer-aided equipment for the analysis of the amplification products.

25. The method of claim 2, further comprising use of computer-aided equipment for the analysis of the amplification products.

26. The method of claim 24, further comprising computer-aided search of a database of nucleotide sequences for identification of the amplification products.

27. The method of claim 25, further comprising computer-aided search of a database of nucleotide sequences for identification of the amplification products.

* * * * *